(12) United States Patent
Dugan

(10) Patent No.: US 10,368,803 B2
(45) Date of Patent: *Aug. 6, 2019

(54) METHODS AND APPARATUS FOR MONITORING AND ENCOURAGING HEALTH AND FITNESS

(71) Applicant: Brian M. Dugan, Sleepy Hollow, NY (US)

(72) Inventor: Brian M. Dugan, Sleepy Hollow, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/992,170

(22) Filed: May 29, 2018

(65) Prior Publication Data

US 2018/0271433 A1   Sep. 27, 2018

Related U.S. Application Data

(63) Continuation of application No. 15/696,174, filed on Sep. 5, 2017, now Pat. No. 9,993,198, which is a (Continued)

(51) Int. Cl.
   *A63B 24/00*   (2006.01)
   *A61B 5/00*    (2006.01)
   (Continued)

(52) U.S. Cl.
   CPC ............ *A61B 5/486* (2013.01); *A61B 5/0022* (2013.01); *A61B 5/1112* (2013.01);
   (Continued)

(58) Field of Classification Search
   CPC ........ A63B 2024/0062; A63B 2024/00; A63B 2024/0087; A63B 24/0062;
   (Continued)

(56) References Cited

U.S. PATENT DOCUMENTS 5,542,420 A * 8/1996 Goldman ............ G06F 19/3418
                                                600/301
5,673,691 A * 10/1997 Abrams ................ G06F 15/025
                                                600/300

(Continued)

OTHER PUBLICATIONS

Tom Foremski, Key Centre for Developing New Internet Devices, Financial Times, Survey London Edition 1 ED, p. 12, Oct. 2, 1996.

(Continued)

*Primary Examiner* — Andrew S Lo
(74) *Attorney, Agent, or Firm* — Dugan & Dugan, PC

(57) ABSTRACT

Methods and apparatus are provided for monitoring and encouraging health and fitness. In accordance with a first aspect, an apparatus is provided that is adapted to assist in weight loss and exercise. The apparatus comprises a personal digital assistant (PDA) having computer program code adapted to assist in at least one of calorie counting, meal selection, meal suggestion, weight monitoring, weight loss or gain monitoring, fat consumption monitoring, sugar consumption monitoring and salt consumption monitoring. The PDA also includes computer program code adapted to display historical data regarding at least one of calorie counting, meal selection, meal suggestion, weight monitoring, weight loss or gain monitoring, fat consumption monitoring, sugar consumption monitoring and salt consumption monitoring. Numerous other embodiments are provided, as are methods, systems and computer program products.

8 Claims, 3 Drawing Sheets

Related U.S. Application Data continuation of application No. 15/071,739, filed on Mar. 16, 2016, now Pat. No. 9,775,560, which is a continuation of application No. 14/923,421, filed on Oct. 26, 2015, now Pat. No. 9,324,246, which is a continuation of application No. 14/585,179, filed on Dec. 23, 2014, now Pat. No. 9,202,013, which is a continuation of application No. 14/314,005, filed on Jun. 24, 2014, now Pat. No. 8,944,960, which is a continuation of application No. 14/095,977, filed on Dec. 3, 2013, now Pat. No. 8,784,272, which is a continuation of application No. 13/708,924, filed on Dec. 7, 2012, now Pat. No. 8,617,032, which is a continuation of application No. 13/305,714, filed on Nov. 28, 2011, now Pat. No. 8,337,367, which is a continuation of application No. 12/979,275, filed on Dec. 27, 2010, now Pat. No. 8,075,451, which is a continuation of application No. 11/676,666, filed on Feb. 20, 2007, now Pat. No. 7,857,730, which is a continuation of application No. 10/945,808, filed on Sep. 21, 2004, now Pat. No. 7,189,191, which is a continuation of application No. 09/702,179, filed on Oct. 30, 2000, now Pat. No. 6,811,516.

(60) Provisional application No. 60/162,502, filed on Oct. 29, 1999.

(51) Int. Cl.
| | |
|---|---|
| *G06F 19/00* | (2018.01) |
| *G06Q 10/08* | (2012.01) |
| *G06Q 30/06* | (2012.01) |
| *G09B 19/00* | (2006.01) |
| *G09B 5/00* | (2006.01) |
| *A61B 5/11* | (2006.01) |
| *G09B 5/02* | (2006.01) |
| *G16H 20/30* | (2018.01) |
| *G16H 40/67* | (2018.01) |
| *G16H 30/20* | (2018.01) |
| *G16H 20/60* | (2018.01) |

(52) U.S. Cl.
CPC .......... *A61B 5/4866* (2013.01); *A61B 5/6824* (2013.01); *A61B 5/6831* (2013.01); *A61B 5/6898* (2013.01); *A61B 5/7475* (2013.01); *A63B 24/0062* (2013.01); *G06F 19/00* (2013.01); *G06F 19/3418* (2013.01); *G06F 19/3475* (2013.01); *G06F 19/3481* (2013.01); *G06F 19/36* (2013.01); *G06Q 10/087* (2013.01); *G06Q 30/0621* (2013.01); *G06Q 30/0623* (2013.01); *G06Q 30/0631* (2013.01); *G06Q 30/0633* (2013.01); *G09B 5/00* (2013.01); *G09B 5/02* (2013.01); *G09B 19/0092* (2013.01); *G16H 20/30* (2018.01); *G16H 20/60* (2018.01); *G16H 30/20* (2018.01); *G16H 40/67* (2018.01); *H05K 999/99* (2013.01); *A61B 2503/12* (2013.01); *A63B 2024/0068* (2013.01)

(58) Field of Classification Search
CPC ............ A63B 2024/0068; A61B 5/486; A61B 5/6898; A61B 5/6831; A61B 5/6824; A61B 5/1112; A61B 5/0022; A61B 5/7475; A61B 5/4866; A61B 2503/12; G61H 20/30; G61H 20/60; G16H 30/20; H05K 999/99; G16H 20/30; G16H 40/67; G16H 30/20; G16H 20/60; G06F 19/00; G06F 19/36; G06F 19/3418; G06F 19/3481; G06F 19/3475; G09B 19/0092; G09B 5/02; G09B 5/00; G06Q 30/0633; G06Q 30/0623; G06Q 30/0631; G06Q 30/0621; G06Q 10/087

See application file for complete search history.

(56) References Cited

U.S. PATENT DOCUMENTS

| | | | |
|---|---|---|---|
| 5,884,281 A | 3/1999 | Smith et al. | |
| 5,890,128 A * | 3/1999 | Diaz | G06F 15/025 705/2 |
| 5,954,510 A | 9/1999 | Merrill et al. | |
| 5,976,083 A * | 11/1999 | Richardson | A61B 5/0245 482/8 |
| 6,038,546 A | 3/2000 | Ferro | |
| 6,341,295 B1 * | 1/2002 | Stotler | G06F 15/025 708/131 |
| 6,458,080 B1 | 10/2002 | Brown | |
| 6,478,736 B1 | 11/2002 | Mault | |
| 6,513,017 B1 | 1/2003 | Howard et al. | |
| 6,553,386 B1 | 4/2003 | Alabaster | |
| 6,635,015 B2 | 10/2003 | Sagel | |
| 6,649,848 B2 | 11/2003 | Kriger | |
| 6,790,178 B1 | 9/2004 | Mault et al. | |
| 6,811,516 B1 | 11/2004 | Dugan | |
| 6,974,078 B1 | 12/2005 | Simon | |
| 7,189,191 B2 | 3/2007 | Dugan | |
| 7,713,171 B1 | 5/2010 | Hickman | |
| 8,398,546 B2 | 3/2013 | Pacione | |
| 8,616,895 B2 | 12/2013 | Brown | |
| 8,641,612 B2 | 2/2014 | Teller et al. | |
| 8,666,469 B2 | 3/2014 | Say et al. | |
| 2002/0107433 A1 | 8/2002 | Mault | |
| 2003/0226695 A1 | 12/2003 | Mault | |
| 2007/0135266 A1 | 6/2007 | Dugan | |
| 2011/0091842 A1 | 4/2011 | Dugan | |
| 2012/0070806 A1 | 3/2012 | Dugan | |
| 2013/0101969 A1 | 4/2013 | Dugan | |
| 2014/0162222 A1 | 6/2014 | Dugan | |
| 2014/0308629 A1 | 10/2014 | Dugan | |
| 2015/0120506 A1 | 4/2015 | Dugan | |
| 2016/0049093 A1 | 2/2016 | Dugan | |
| 2016/0192875 A1 | 7/2016 | Dugan | |
| 2017/0360359 A1 | 12/2017 | Dugan | |

OTHER PUBLICATIONS

Office Action of U.S. Appl. No. 09/702,179 dated Sep. 29, 2003.
Mar. 29, 2004 Response to Office Action of U.S. Appl. No. 09/702,179 dated Sep. 29, 2003.
Notice of Allowance of U.S. Appl. No. 09/702,179 dated Jun. 21, 2004.
Preliminary Amendment of U.S. Appl. No. 10/945,808 dated Jul. 11, 2005.
Office Action of U.S. Appl. No. 10/945,808 dated Apr. 14, 2006.
Sep. 14, 2006 Response to Office Action of U.S. Appl. No. 10/945,808 dated Apr. 14, 2006.
Notice of Allowance of U.S. Appl. No. 10/945,808 dated Nov. 3, 2006.
Office Action of U.S. Appl. No. 11/676,666 dated Sep. 18, 2008.
Feb. 18, 2009 Response to Office Action of U.S. Appl. No. 11/676,666 dated Sep. 18, 2008.
Office Action of U.S. Appl. No. 11/676,666 dated Jun. 10, 2009.
Nov. 10, 2009 Response to Office Action of U.S. Appl. No. 11/676,666 dated Jun. 10, 2009.
Final Office Action of U.S. Appl. No. 11/676,666 dated Feb. 5, 2010.
May 5, 2010 Response to Final Office Action of U.S. Appl. No. 11/676,666 dated Feb. 5, 2010.
Interview Summary of U.S. Appl. No. 11/676,666, filed Jul. 9, 2010.
Advisory Action of U.S. Appl. No. 11/676,666 dated Jul. 12, 2010.
Amendment submitted with RCE of U.S. Appl. No. 11/676,666, filed Aug. 5, 2010.

(56) References Cited

OTHER PUBLICATIONS

Examiner Interview Summary of U.S. Appl. No. 11/676,666 dated Aug. 5, 2010.
Interview Summary of U.S. Appl. No. 11/676,666, filed Aug. 11, 2010.
Restriction Requirement of U.S. Appl. No. 10/945,808 dated Aug. 22, 2005.
Sep. 22, 2005 Response to Restriction Requirement of U.S. Appl. No. 10/945,808 dated Aug. 22, 2005.
Restriction Requirement of U.S. Appl. No. 10/945,808 dated Jan. 10, 2006.
Feb. 10, 2006 Response to Restriction Requirement of U.S. Appl. No. 10/945,808 dated Jan. 10, 2006.
Notice of Allowance of U.S. Appl. No. 11/676,666 dated Aug. 19, 2010.
Office Action of U.S. Appl. No. 12/979,275 dated Mar. 7, 2011.
Sep. 7, 2011 Response to Office Action of U.S. Appl. No. 12/979,275 dated Mar. 7, 2011.
Notice of Allowance of U.S. Appl. No. 12/979,275 dated Sep. 30, 2011.
Office Action of U.S. Appl. No. 13/305,714 dated Mar. 9, 2012.
Sep. 10, 2012 Response to Office Action of U.S. Appl. No. 13/305,714 dated Mar. 9, 2012.
Notice of Allowance of U.S. Appl. No. 13/305,714 dated Nov. 14, 2012.
Office Action of U.S. Appl. No. 13/708,924 dated Jan. 31, 2013.
Jul. 31, 2013 Reply to Jan. 31, 2013 Office Action of U.S. Appl. No. 13/708,924.
Notice of Allowance of U.S. Appl. No. 13/708,924 dated Aug. 27, 2013.
Notice of Allowance of U.S. Appl. No. 14/095,977 dated Mar. 18, 2014.
Preliminary Amendment of U.S. Appl. No. 14/314,005, filed Jul. 18, 2014.
Notice of Allowance and Applicant-Initiated Interview Summary of U.S. Appl. No. 14/314,005, filed Sep. 18, 2014.
Non-Final Office Action of U.S. Appl. No. 14/582,179, dated Feb. 13, 2015.
Jul. 13, 2015 Reply to Feb. 13, 2015 Non-Final Office Action of U.S. Appl. No. 14/582,179.
Notice of Allowance of U.S. Appl. No. 14/582,179, dated Jul. 27, 2015.
Office Action of U.S. Appl. No. 14/923,421 dated Nov. 18, 2015.
Dec. 31, 2015 Reply to Nov. 18, 2015 Office Action of U.S. Appl. No. 14/923,421.
Notice of Allowance of U.S. Appl. No. 14/923,421 dated Jan. 13, 2016.
Non-Final Office Action of U.S. Appl. No. 15/071,739 dated Apr. 13, 2016.
Oct. 13, 2016 Reply and Terminal Disclaimers to Apr. 13, 2016 Non-Final Office Action of U.S. Appl. No. 15/071,739.
Final Office Action of U.S. Appl. No. 15/071,739 dated Nov. 15, 2016.
Terminal Disclaimers Filed in Response to Final Office Action of U.S. Appl. No. 15/071,739, filed Mar. 15, 2017.
Notice of Allowance of U.S. Appl. No. 15/071,739 dated Jun. 1, 2017.
Non-Final Office Action of U.S. Appl. No. 15/696,174 dated Sep. 26, 2017.
Dec. 26, 2017 Reply to Sep. 26, 2017 Non-Final Office Action of U.S. Appl. No. 15/696,174.
Notice of Allowance of U.S. Appl. No. 15/696,174 dated Feb. 13, 2018.

\* cited by examiner

US 10,368,803 B2

METHODS AND APPARATUS FOR MONITORING AND ENCOURAGING HEALTH AND FITNESS

This application is a continuation of and claims priority from U.S. patent application Ser. No. 15/696,174 filed Sep. 5, 2017, and titled "METHODS AND APPARATUS FOR MONITORING AND ENCOURAGING HEALTH AND FITNESS", which is a continuation of and claims priority from U.S. patent application Ser. No. 15/071,739 filed Mar. 16, 2016, now U.S. Pat. No. 9,775,560 and titled "METHODS AND APPARATUS FOR MONITORING AND ENCOURAGING HEALTH AND FITNESS", which is a continuation of and claims priority from U.S. patent application Ser. No. 14/923,421 filed Oct. 26, 2015, now U.S. Pat. No. 9,324,246 and titled "METHODS AND APPARATUS FOR MONITORING AND ENCOURAGING HEALTH AND FITNESS", which is a continuation of and claims priority from U.S. patent application Ser. No. 14/582,179 filed Dec. 23, 2014, now U.S. Pat. No. 9,202,013 and titled "METHODS AND APPARATUS FOR MONITORING AND ENCOURAGING HEALTH AND FITNESS", which is a continuation of and claims priority from U.S. patent application Ser. No. 14/314,005 filed Jun. 24, 2014, now U.S. Pat. No. 8,944,960 and titled "METHODS AND APPARATUS FOR MONITORING AND ENCOURAGING HEALTH AND FITNESS", which is a continuation of and claims priority from U.S. patent application Ser. No. 14/095,977 filed Dec. 3, 2013, now U.S. Pat. No. 8,784,272 and titled "METHODS AND APPARATUS FOR MONITORING AND ENCOURAGING HEALTH AND FITNESS", which is a continuation of and claims priority from U.S. patent application Ser. No. 13/708,924 filed Dec. 7, 2012, now U.S. Pat. No. 8,617,032 and titled "METHODS AND APPARATUS FOR MONITORING AND ENCOURAGING HEALTH AND FITNESS", which is a continuation of and claims priority from U.S. patent application Ser. No. 13/305,714 filed Nov. 28, 2011, now U.S. Pat. No. 8,337,367 and titled "METHODS AND APPARATUS FOR MONITORING AND ENCOURAGING HEALTH AND FITNESS", which is a continuation of and claims priority from U.S. patent application Ser. No. 12/979,275 filed Dec. 27, 2010, now U.S. Pat. No. 8,075,451 and titled "METHODS AND APPARATUS FOR MONITORING AND ENCOURAGING HEALTH AND FITNESS", which is a continuation of and claims priority from U.S. patent application Ser. No. 11/676,666 filed Feb. 20, 2007, now U.S. Pat. No. 7,857,730, and titled "METHODS AND APPARATUS FOR MONITORING AND ENCOURAGING HEALTH AND FITNESS", which is a continuation of and claims priority from U.S. patent application Ser. No. 10/945,808 filed Sep. 21, 2004, now U.S. Pat. No. 7,189,191, and titled "METHODS AND APPARATUS FOR MONITORING AND ENCOURAGING HEALTH AND FITNESS", which is a continuation of and claims priority from U.S. patent application Ser. No. 09/702,179 filed Oct. 30, 2000, now U.S. Pat. No. 6,811,516, and titled "METHODS AND APPARATUS FOR MONITORING AND ENCOURAGING HEALTH AND FITNESS", which claims priority from U.S. Provisional Patent Application Ser. No. 60/162,502, filed Oct. 29, 1999, and titled "METHODS OF CONDUCTING INTERNET COMMERCE". All of the above applications are hereby incorporated by reference herein in their entirety.

FIELD OF THE INVENTION

The present application relates to methods and apparatus for monitoring and encouraging health and fitness.

BACKGROUND OF THE INVENTION

A fitness craze has recently swept the United States and many other countries. From fat-free potato chips to treadmills, people around the world have become obsessed with weight loss and healthy living. Accordingly, record numbers of new fitness products/exercise equipment have emerged to meet this obsession (including stair climbers, treadmills, recumbent bicycles, ski machines, and the like). However, no convenient mechanism has been developed for monitoring and encouraging health and fitness.

SUMMARY OF THE INVENTION

To overcome the needs of the prior art, methods and apparatus are provided for monitoring and encouraging health and fitness. In accordance with a first aspect of the invention, an apparatus is provided that is adapted to assist in weight loss and exercise. The apparatus comprises a personal digital assistant (PDA) having computer program code adapted to assist in at least one of calorie counting, meal selection, meal suggestion, weight monitoring, weight loss or gain monitoring, fat consumption monitoring, sugar consumption monitoring and salt consumption monitoring. The PDA also includes computer program code adapted to display historical data regarding at least one of calorie counting, meal selection, meal suggestion, weight monitoring, weight loss or gain monitoring, fat consumption monitoring, sugar consumption monitoring and salt consumption monitoring. Numerous other embodiments are provided, as are methods, systems and computer program products. Each computer program product may be carried by a medium readable by a computer (e.g., a carrier wave signal, a floppy disc, a hard drive, a random access memory, etc.).

Other objects, features and aspects of the present invention will become more fully apparent from the following detailed description of the preferred embodiments, the appended claims and the accompanying drawings.

DETAILED DESCRIPTION

Figure 1:
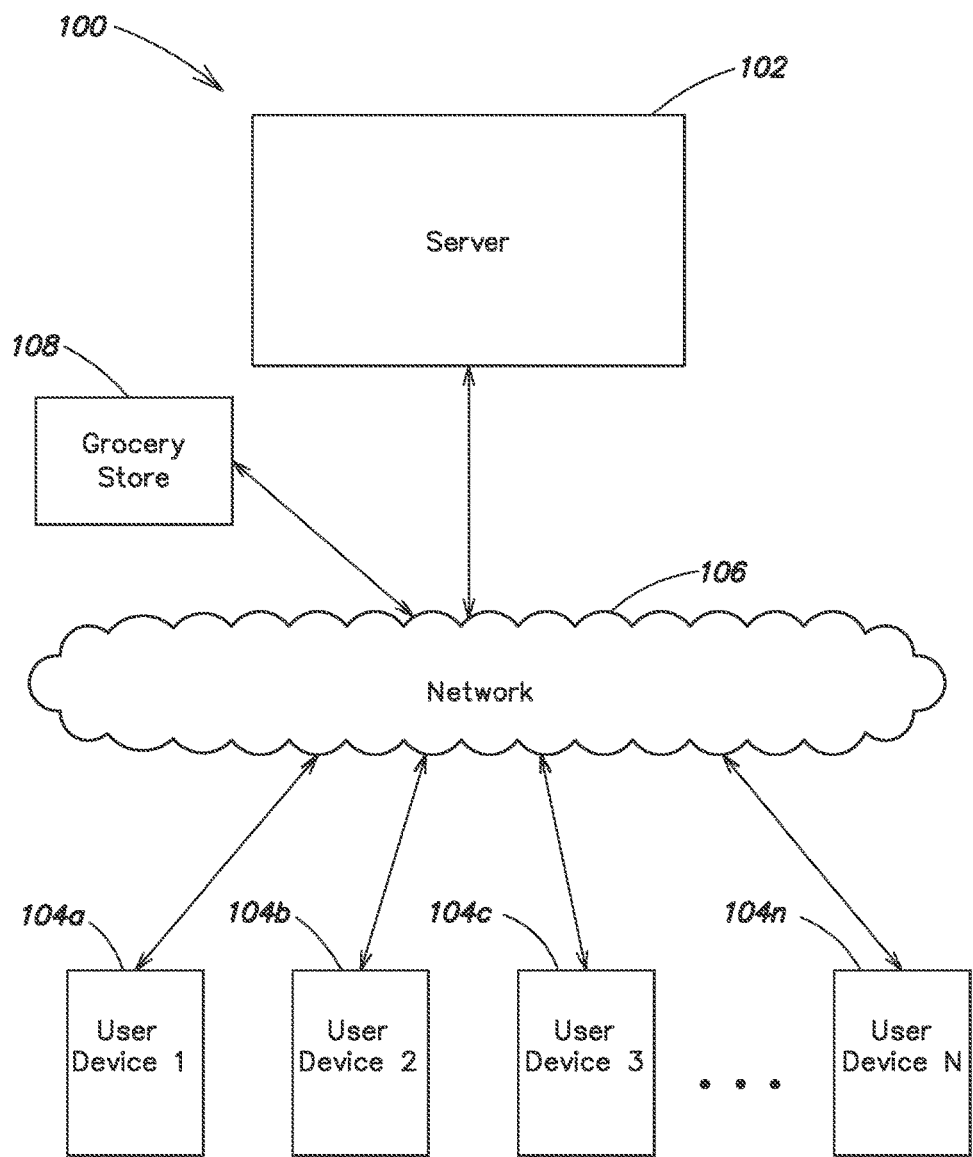
FIG. 1 is a schematic diagram of an exemplary system for monitoring and encouraging health and fitness.

FIG. 1 is a schematic diagram of an exemplary system 100 for monitoring and encouraging health and fitness. The system 100 includes a server 102 that may communicate with one or more user devices 104a-n via a network 106. As shown in FIG. 1, a grocery store 108 may also be in communication with the server 102 and/or with one or more of the user devices 104a-n via the network 106. Any other party such as a restaurant, a catering service, and/or any other relevant person or entity may be in communication with the server 102 in addition to, or in place of the grocery store 108. It will be understood that devices in communication need not be in continuous communication and actually may refrain from exchanging data/information most of the time. Additionally, devices may be in communication even though one or more steps must be performed before the devices may communicate (e.g., dialing a network service provider, connecting to a network service provider, logging onto a Web site, etc.).

The server 102 may comprise any conventional server (e.g., one or more conventional microprocessors) having computer program code contained therein as described below. Each user device 104a-n may comprise a desk top computer, a lap top computer, a set top box, a personal digital assistant (PDA), an internet-capable telephone device and/or any other device capable of communicating with the server 102 via the network 106, and each user device 104a-n may have computer program code contained therein as described below. The network 106 may comprise a local area network (LAN), a wide area network (WAN), the Internet, an intranet, an extranet or any other network. In general one or more of the user devices 104a-n, the grocery store 108, and/or any other relevant third party may communicate with the server 102 or amongst one another via any communications medium (e.g., via telephone, via facsimile, via mail, etc.).

As stated, the server 102 and/or one or more of the user devices 104a-n may contain computer program code adapted to direct the server 102 and/or the one or more user devices 104a-n in accordance with one or more embodiments of the invention.

Figure 2:
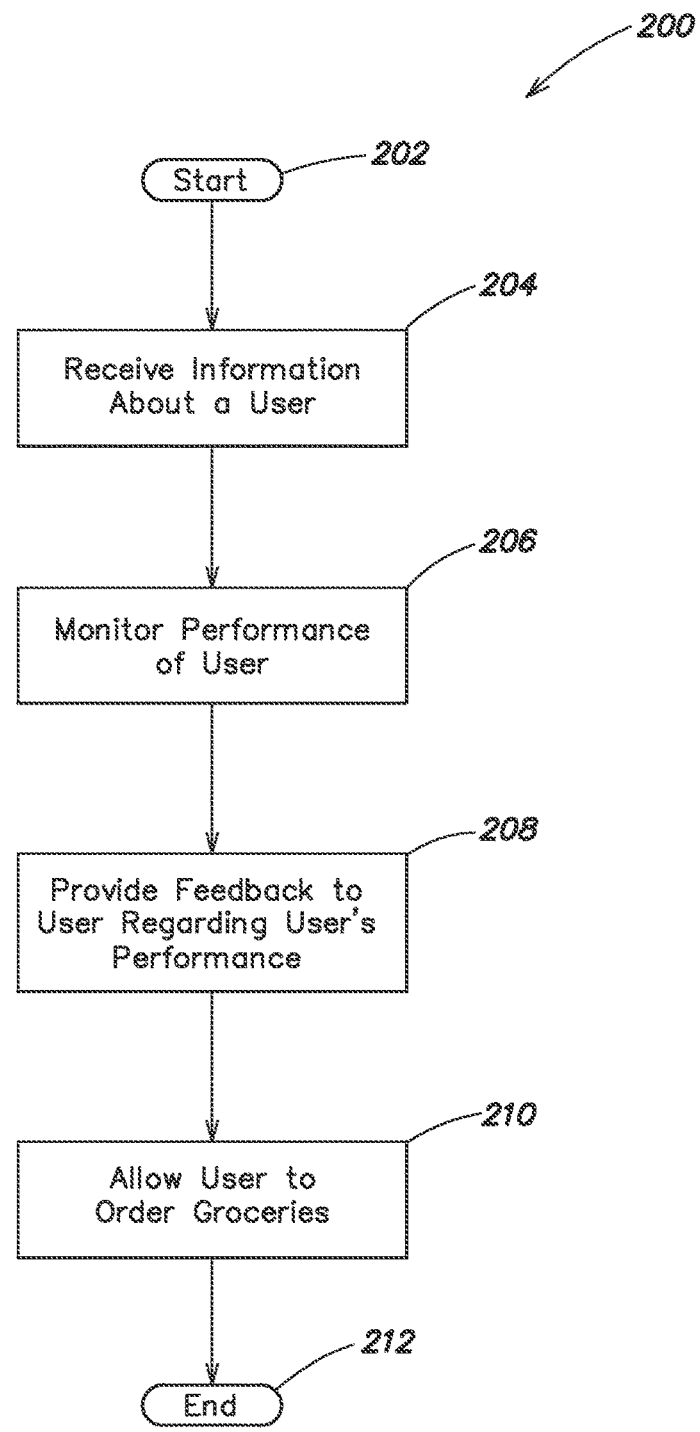
FIG. 2 is a flowchart of a first exemplary process of the system of FIG. 1.

FIG. 2 is a flowchart of a first exemplary process 200 of the system 100. With reference to FIG. 2, in step 202, the process 200 begins. In step 204, the server 102 receives information about a user. For example, if the server 102 is a Web server, the user may employ one of the user devices 104a-n to log-on to a Web site administered by the server 102, and to provide information to the server 102. Relevant information may include any type of demographic information (e.g., age, weight, height, sex, etc.), geographic/address information (e.g., where the user lives, contact information, etc.), goals or objectives of the user (e.g., weight loss, healthier diet, exercise objectives, etc.) or any other relevant information. In general, information about the user may be provided to the server 102 by any mechanism (e.g., via mail, via e-mail, via telephone, via cellular telephone, via facsimile, etc.). For example, information may be received via one or more HTTP transmissions or via some other communications protocol.

In step 206, the server 102 monitors the performance of the user (e.g., receives information from one or more of the user devices 104a-n about the user's food intake and/or exercise level and/or generates historical information about the user's performance). In step 208, the server 102 provides feedback to the user based on the monitored performance of the user (e.g., encouragement to exercise more, not to eat certain foods, to eat certain foods, etc.). The feedback may be provided at any time (e.g., periodically, randomly, etc.) and by any means (e.g., via mail, via e-mail, via facsimile, via telephone, etc.).

In step 210, the user (optionally) may employ one or more of the user devices 104a-n to order groceries from the grocery store 108 (e.g., in accordance with the dietary goals of the user). For example, the system 100 may be configured so as to:

maintain on a PDA a list of grocery items purchased by a shopper;
display on the PDA at least one of the grocery items within the maintained list of grocery items;
allow selection of one or more of the displayed previously purchased grocery items;
display at least one of the grocery items within the maintained a list of grocery items based on prior use patterns of the shopper;
display a message that indicates that, based on prior use patterns of the shopper, at least one of the grocery items within the maintained list of grocery items should be purchased by the shopper;
e-mail the shopper;
display on a PDA a list of user-selectable grocery items;
allow selection of at least one of the displayed selectable grocery items;
display at least one characteristic of a selected grocery item (e.g., a characteristic selected from the group consisting of calories, fat content, salt content, cholesterol content, whether organically grown, whether low fat, whether suitable for diabetics, whether Kosher, price, size, shelf life and brand name);
display a comparison of at least one characteristic of a plurality of selected grocery items;
allow selection of the at least one characteristic.
rank a plurality of selected grocery items based on the at least one characteristic.
maintain on a PDA a list of grocery items purchased by a shopper;
generate a report based on the list of purchased grocery items;
generate a report selected from the group consisting of calorie consumption, fat consumption, sugar consumption, salt consumption and grocery cost;
e-mail a report;
generate a report periodically;
display on a PDA a list of prepared foods;
allow selection of at least one prepared food;
display a recipe for each selected prepared food;
display at least one user-selectable grocery item that is an ingredient of the recipe;
display the cost of preparing each selected prepared food based on the cost of user-selected ingredients.
display at least one user-selectable ingredient for the recipe based on a maintained list of grocery items purchased by a shopper;
display a date when each user-selected ingredient was previously purchased by the shopper; and/or
provide a link to a food preparation WEB site capable of generating a price quotation for the preparation of at least one selected prepared food.

In step 212, the process 200 ends.

The foregoing description discloses only exemplary embodiments of the invention, modifications of the above disclosed apparatus and method which fall within the scope of the invention will be readily apparent to those of ordinary skill in the art. For instance, in at least one embodiment of the invention, one or more of the user devices 104a-n is a personal digital assistant (PDA) having an application (e.g., computer program code) adapted to assist in calorie counting (e.g., keeping track of caloric intake), meal selection, meal suggestion, weight monitoring (e.g., via user entry or via a download from an electronic scale), weight loss or gain monitoring, fat consumption monitoring, sugar consumption monitoring and salt consumption monitoring. The one or more PDAs may include computer program code adapted to display historical data regarding at least one of calorie counting, meal selection, meal suggestion, weight monitoring, weight loss or gain monitoring, fat consumption monitoring, sugar consumption monitoring and salt consumption monitoring.

Figure 3:
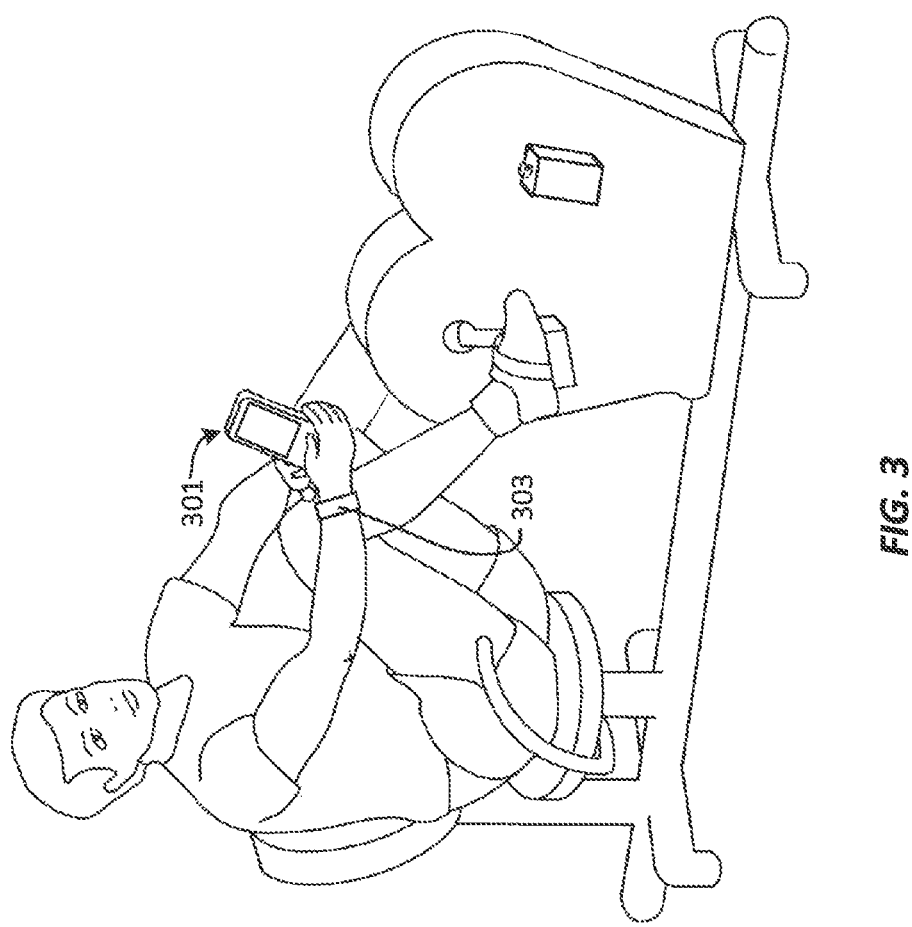
FIG. 3 is a schematic diagram of an example embodiment of a web-enabled, handheld electronic device and wrist worn monitor.

Exercise suggestions, exercise statistics (e.g., time exercised, distance run, type of exercise performed, historical data, etc.) may be stored/accessed via one or more of the user devices 104*a*-*n*. The information may be stored locally (e.g., within the PDA) or remotely (e.g., within the server 102). Additionally, a pulse monitor or other monitor may be provided that interfaces the PDA (e.g., by modifying the PDA if necessary to allow such an interface) and that automatically provides exercise information and/or calories-burned information to the PDA. A comparison of calorie intake versus calories burned may be automatically generated at any time (e.g., after a meal, at the end of the day, after exercise, etc.). Inspirational messages may be displayed (e.g., during exercise, prior to meal time, automatically if desired, etc.) to help with weight loss/exercise performance. Each PDA may be provided with a video game such as described in U.S. Pat. No. 5,947,868 (which is hereby incorporated by reference in its entirety) to further inspire exercise. For example, FIG. 3 illustrates a web-enabled, handheld electronic device 301 in communication with a wrist worn monitor 303 (e.g., a wrist band).

Each PDA may store, for example, grocery lists and may download information from a WEB site regarding suitable meals, products, etc., that are consistent with a user's diet and exercise goals. The WEB site may include a health food line such as WEIGHT WATCHER'S™, or any of the other grocery concepts described herein.

Accordingly, while the present invention has been disclosed in connection with the preferred embodiments thereof, it should be understood that other embodiments may fall within the spirit and scope of the invention, as defined by the following claims.

What is claimed is:

1. A system, comprising:
   a wearable monitor configured to monitor biometric information of a user as the user exercises, wherein the wearable monitor is configured to transmit the biometric information wirelessly as the user exercises; and
   a handheld electronic device associated with the user, the handheld electronic device being web-enabled, and having computer program code stored therein that, when executed by the handheld electronic device, causes the handheld electronic device to:
   receive the biometric information transmitted by the wearable monitor as the user exercises;
   determine exercise level information based on the received biometric information;
   transmit the exercise level information determined from the received biometric information to a remotely-located server;
   transmit geographic information about the user to the remotely-located server;
   receive input from the user indicating a diet and exercise goal;
   transmit the diet and exercise goal to the remotely-located server;
   obtain product information for a product determined by the remotely-located server to be consistent with the diet and exercise goal, such determination being based on the exercise level information transmitted to the remotely-located server; and
   present the product information to the user on the handheld electronic device as being consistent with the diet and exercise goal.

2. The system of claim 1, wherein the computer program code stored in the handheld electronic device, when executed by the handheld electronic device, further causes the handheld electronic device to facilitate a purchase of the product by the user.

3. The system of claim 1, wherein the computer program code stored in the handheld electronic device, when executed by the handheld electronic device, further causes the handheld electronic device to transmit food intake information to the remotely-located server.

4. The system of claim 3, wherein the computer program code stored in the handheld electronic device, when executed by the handheld electronic device, further causes the handheld electronic device to monitor food intake information of the user.

5. The system of claim 1, wherein the computer program code stored in the handheld electronic device, when executed by the handheld electronic device, further causes the handheld electronic device to provide inspirational messages to the user during exercise.

6. The system of claim 1, wherein the computer program code stored in the handheld electronic device, when executed by the handheld electronic device, further causes the handheld electronic device to provide inspirational messages to the user prior to at least one meal time.

7. The system of claim 1, wherein the computer program code stored in the handheld electronic device, when executed by the handheld electronic device, further causes the handheld electronic device to provide inspirational messages to the user automatically.

8. The system of claim 1, wherein the computer program code stored in the handheld electronic device, when executed by the handheld electronic device, further causes the handheld electronic device to provide a video game, and use monitored exercise level information to affect the video game.

* * * * *